(12) United States Patent
Soto Del Valle et al.

(10) Patent No.: US 11,432,822 B2
(45) Date of Patent: Sep. 6, 2022

(54) INTRAVASCULAR IMPLANT DEPLOYMENT SYSTEM

(71) Applicant: DePuy Synthes Products, Inc., Raynham, MA (US)

(72) Inventors: Ariel Soto Del Valle, Raynham, MA (US); Juan Lorenzo, Raynham, MA (US); Lacey Gorochow, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 16/791,578

(22) Filed: Feb. 14, 2020

(65) Prior Publication Data

US 2021/0251635 A1 Aug. 19, 2021

(51) Int. Cl.
*A61B 17/12* (2006.01)
*A61M 25/00* (2006.01)
*A61B 17/00* (2006.01)

(52) U.S. Cl.
CPC .. *A61B 17/12172* (2013.01); *A61B 17/12113* (2013.01); *A61M 25/0021* (2013.01);
(Continued)

(58) Field of Classification Search
CPC ........ A61B 17/12172; A61B 17/12113; A61B 2017/00323; A61B 2017/12054;
(Continued)

(56) References Cited

U.S. PATENT DOCUMENTS

| 3,429,408 A | 2/1969 | Maker et al. |
| 5,108,407 A | 4/1992 | Geremia et al. |

(Continued)

FOREIGN PATENT DOCUMENTS

| EP | 1985244 A2 | 10/2008 |
| EP | 2498691 | 9/2012 |

(Continued)

OTHER PUBLICATIONS

Extended European Search Report issued in European Patent Application No. 21 15 6857 dated Jun. 22, 2021, pp. 1-9.
(Continued)

*Primary Examiner* — Katherine M Shi
*Assistant Examiner* — Paige A Codrington
(74) *Attorney, Agent, or Firm* — Troutman Pepper Hamilton Sanders LLP

(57) ABSTRACT

An example system for deploying an intrasaccular implant to occlude an aneurysm can include the intrasaccular implant with a securing ring thereon, a pusher, a securing wire with an extended securing feature thereon, and a pull wire. The system can be sized to be delivered intravascularly within a microcatheter. During delivery and manipulation of the implant, the securing ring can be held between the pusher and the securing feature of the securing wire with the securing wire and pull wire extended through securing ring. To deploy the implant, the pull wire can be retracted proximally to thereby allow the securing feature to pass through the securing ring and release the implant. The pusher can include a hypotube and/or an extended pushing feature on the securing wire.

18 Claims, 9 Drawing Sheets

(52) U.S. Cl.
CPC ........... *A61B 2017/00323* (2013.01); *A61B 2017/12054* (2013.01); *A61M 2025/0042* (2013.01)

(58) Field of Classification Search
CPC . A61B 2017/12022; A61B 2017/1205; A61M 25/0021; A61M 25/0013; A61M 25/0054; A61M 2025/0042
USPC ........................................................ 606/200
See application file for complete search history.

(56) References Cited

U.S. PATENT DOCUMENTS

| | | | |
|---|---|---|---|
| 5,122,136 A | 6/1992 | Guglielmi et al. |
| 5,250,071 A | 10/1993 | Palermo |
| 5,263,964 A | 11/1993 | Purdy |
| 5,334,210 A | 8/1994 | Gianturco |
| 5,350,397 A | 9/1994 | Palermo et al. |
| 5,382,259 A | 1/1995 | Phelps et al. |
| 5,484,409 A | 1/1996 | Atkinson et al. |
| 5,569,221 A | 10/1996 | Houser et al. |
| 5,899,935 A | 5/1999 | Ding |
| 5,925,059 A | 7/1999 | Palermo et al. |
| 6,113,622 A | 9/2000 | Hieshima |
| 6,203,547 B1 | 3/2001 | Nguyen et al. |
| 6,391,037 B1 | 5/2002 | Greenhalgh |
| 6,454,780 B1 | 9/2002 | Wallace |
| 6,506,204 B2 | 1/2003 | Mazzocchi |
| 6,561,988 B1 | 5/2003 | Turturro et al. |
| 7,367,987 B2 | 5/2008 | Balgobin et al. |
| 7,371,251 B2 | 5/2008 | Mitelberg et al. |
| 7,371,252 B2 | 5/2008 | Balgobin et al. |
| 7,377,932 B2 | 5/2008 | Mitelberg et al. |
| 7,708,754 B2 | 5/2010 | Balgobin et al. |
| 7,708,755 B2 | 5/2010 | Davis, III et al. |
| 7,799,052 B2 | 9/2010 | Balgobin et al. |
| 7,811,305 B2 | 10/2010 | Balgobin et al. |
| 7,819,891 B2 | 10/2010 | Balgobin et al. |
| 7,819,892 B2 | 10/2010 | Balgobin et al. |
| 7,901,444 B2 | 3/2011 | Slazas |
| 7,985,238 B2 | 7/2011 | Balgobin et al. |
| 8,062,325 B2 | 11/2011 | Mitelberg et al. |
| 8,333,796 B2 | 12/2012 | Tompkins et al. |
| 9,155,540 B2 | 10/2015 | Lorenzo |
| 9,232,992 B2 | 1/2016 | Heidner |
| 9,314,326 B2 | 4/2016 | Wallace et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,120 B2 | 5/2017 | Lagodzki et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Paterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 9,918,718 B2 | 3/2018 | Lorenzo |
| 10,285,710 B2 | 5/2019 | Lorenzo et al. |
| 10,292,851 B2 | 5/2019 | Gorochow |
| 10,420,563 B2 | 9/2019 | Hebert et al. |
| 10,517,604 B2 | 12/2019 | Bowman et al. |
| 10,668,258 B1 | 6/2020 | Calhoun et al. |
| 10,806,402 B2 | 10/2020 | Cadieu et al. |
| 10,806,461 B2 | 10/2020 | Lorenzo |
| 2001/0049519 A1 | 12/2001 | Holman et al. |
| 2002/0072705 A1 | 6/2002 | Vrba et al. |
| 2002/0165569 A1 | 11/2002 | Ramzipoor et al. |
| 2003/0009208 A1 | 1/2003 | Snyder et al. |
| 2004/0034363 A1 | 2/2004 | Wilson et al. |
| 2004/0059367 A1 | 3/2004 | Davis et al. |
| 2004/0087964 A1 | 5/2004 | Diaz et al. |
| 2006/0025801 A1* | 2/2006 | Lulo ............... A61B 17/1214 606/200 |
| 2006/0064151 A1 | 3/2006 | Guterman |
| 2006/0100687 A1 | 5/2006 | Fahey et al. |
| 2006/0116711 A1 | 6/2006 | Elliott et al. |
| 2006/0116714 A1* | 6/2006 | Sepetka ........... A61B 17/12022 606/200 |
| 2006/0135986 A1* | 6/2006 | Wallace ........... A61B 17/12154 606/200 |
| 2006/0206139 A1* | 9/2006 | Tekulve ........... A61B 17/12131 606/200 |
| 2006/0247677 A1* | 11/2006 | Cheng ............. A61B 17/1214 606/200 |
| 2006/0276824 A1 | 12/2006 | Mitelberg et al. |
| 2006/0276825 A1 | 12/2006 | Mitelberg et al. |
| 2006/0276826 A1 | 12/2006 | Mitelberg et al. |
| 2006/0276827 A1 | 12/2006 | Mitelberg et al. |
| 2006/0276830 A1 | 12/2006 | Balgobin et al. |
| 2006/0276833 A1 | 12/2006 | Balgobin et al. |
| 2007/0010850 A1 | 1/2007 | Balgobin et al. |
| 2007/0055302 A1* | 3/2007 | Henry ............. A61B 17/12154 606/200 |
| 2007/0083132 A1 | 4/2007 | Sharrow |
| 2007/0233168 A1 | 10/2007 | Davis et al. |
| 2007/0270903 A1 | 11/2007 | Davis, III et al. |
| 2008/0027561 A1 | 1/2008 | Mitelberg et al. |
| 2008/0045997 A1 | 2/2008 | Balgobin et al. |
| 2008/0097462 A1* | 4/2008 | Mitelberg ................ A61F 2/95 606/108 |
| 2008/0281350 A1 | 11/2008 | Sepetka |
| 2008/0300616 A1* | 12/2008 | Que ............... A61B 17/12113 606/191 |
| 2008/0306503 A1 | 12/2008 | Que et al. |
| 2009/0062726 A1 | 3/2009 | Ford et al. |
| 2009/0312748 A1 | 12/2009 | Johnson et al. |
| 2010/0114017 A1 | 5/2010 | Lenker et al. |
| 2010/0324649 A1 | 12/2010 | Mattsson |

(56) References Cited

U.S. PATENT DOCUMENTS

| | | | |
|---|---|---|---|
| 2011/0202085 A1* | 8/2011 | Loganathan | A61B 17/12022 606/200 |
| 2011/0295303 A1 | 12/2011 | Freudenthal | |
| 2012/0035707 A1 | 2/2012 | Mitelberg et al. | |
| 2012/0041472 A1 | 2/2012 | Tan et al. | |
| 2012/0283768 A1 | 11/2012 | Cox et al. | |
| 2013/0066413 A1 | 3/2013 | Jin et al. | |
| 2014/0058435 A1 | 2/2014 | Jones et al. | |
| 2014/0135812 A1 | 5/2014 | Divino et al. | |
| 2014/0200607 A1 | 7/2014 | Sepetka et al. | |
| 2014/0277084 A1 | 9/2014 | Mirigian et al. | |
| 2014/0277085 A1 | 9/2014 | Mirigian et al. | |
| 2014/0277092 A1 | 9/2014 | Teoh et al. | |
| 2014/0277093 A1 | 9/2014 | Guo et al. | |
| 2015/0005808 A1 | 1/2015 | Chouinard et al. | |
| 2015/0025562 A1 | 1/2015 | Dinh et al. | |
| 2015/0182227 A1 | 7/2015 | Le et al. | |
| 2015/0230802 A1 | 8/2015 | Lagodzki et al. | |
| 2015/0335333 A1* | 11/2015 | Jones | A61B 17/12154 606/200 |
| 2016/0008003 A1* | 1/2016 | Kleshinski | A61B 17/12172 606/200 |
| 2016/0022275 A1 | 1/2016 | Garza | |
| 2016/0022445 A1* | 1/2016 | Ruvalcaba | A61F 2/82 606/198 |
| 2016/0157869 A1* | 6/2016 | Elgard et al. | A61B 17/1214 606/200 |
| 2016/0228125 A1 | 8/2016 | Pederson, Jr. et al. | |
| 2016/0310304 A1 | 10/2016 | Mialhe | |
| 2016/0346508 A1 | 12/2016 | Williams et al. | |
| 2017/0007264 A1 | 1/2017 | Cruise et al. | |
| 2017/0007265 A1 | 1/2017 | Guo et al. | |
| 2017/0020670 A1 | 1/2017 | Murray et al. | |
| 2017/0020700 A1 | 1/2017 | Bienvenu et al. | |
| 2017/0027640 A1 | 2/2017 | Kunis et al. | |
| 2017/0027692 A1 | 2/2017 | Bonhoeffer et al. | |
| 2017/0027725 A1 | 2/2017 | Argentine | |
| 2017/0035436 A1 | 2/2017 | Morita | |
| 2017/0035567 A1 | 2/2017 | Duffy | |
| 2017/0042548 A1 | 2/2017 | Lam | |
| 2017/0049596 A1 | 2/2017 | Schabert | |
| 2017/0071737 A1 | 3/2017 | Kelley | |
| 2017/0072452 A1 | 3/2017 | Monetti et al. | |
| 2017/0079671 A1 | 3/2017 | Morero et al. | |
| 2017/0079680 A1 | 3/2017 | Bowman | |
| 2017/0079766 A1 | 3/2017 | Wang et al. | |
| 2017/0079767 A1 | 3/2017 | Leon-Yip | |
| 2017/0079812 A1 | 3/2017 | Lam et al. | |
| 2017/0079817 A1 | 3/2017 | Sepetka et al. | |
| 2017/0079819 A1 | 3/2017 | Pung et al. | |
| 2017/0079820 A1 | 3/2017 | Lam et al. | |
| 2017/0086851 A1 | 3/2017 | Wallace et al. | |
| 2017/0086996 A1 | 3/2017 | Peterson et al. | |
| 2017/0095258 A1* | 4/2017 | Tassoni | A61B 17/12145 |
| 2017/0095259 A1 | 4/2017 | Tompkins et al. | |
| 2017/0100126 A1 | 4/2017 | Bowman et al. | |
| 2017/0100141 A1 | 4/2017 | Morero et al. | |
| 2017/0100143 A1 | 4/2017 | Granfield | |
| 2017/0100183 A1 | 4/2017 | Iaizzo et al. | |
| 2017/0113023 A1 | 4/2017 | Steingisser et al. | |
| 2017/0147765 A1 | 5/2017 | Mehta | |
| 2017/0151032 A1 | 6/2017 | Loisel | |
| 2017/0165062 A1 | 6/2017 | Rothstein | |
| 2017/0165065 A1 | 6/2017 | Rothstein et al. | |
| 2017/0165454 A1 | 6/2017 | Tuohy et al. | |
| 2017/0172581 A1 | 6/2017 | Bose et al. | |
| 2017/0172766 A1 | 6/2017 | Vong et al. | |
| 2017/0172772 A1 | 6/2017 | Khenansho | |
| 2017/0189033 A1 | 7/2017 | Sepetka et al. | |
| 2017/0189035 A1 | 7/2017 | Porter | |
| 2017/0215902 A1 | 8/2017 | Leynov et al. | |
| 2017/0216484 A1 | 8/2017 | Cruise et al. | |
| 2017/0224350 A1 | 8/2017 | Shimizu et al. | |
| 2017/0224355 A1 | 8/2017 | Bowman et al. | |
| 2017/0224467 A1 | 8/2017 | Piccagli et al. | |
| 2017/0224511 A1 | 8/2017 | Dwork et al. | |
| 2017/0224953 A1 | 8/2017 | Tran et al. | |
| 2017/0231749 A1 | 8/2017 | Perkins et al. | |
| 2017/0245864 A1 | 8/2017 | Franano et al. | |
| 2017/0245885 A1 | 8/2017 | Lenker | |
| 2017/0252064 A1 | 9/2017 | Staunton | |
| 2017/0258476 A1 | 9/2017 | Hayakawa et al. | |
| 2017/0265983 A1 | 9/2017 | Lam et al. | |
| 2017/0281192 A1 | 10/2017 | Tieu et al. | |
| 2017/0281331 A1 | 10/2017 | Perkins et al. | |
| 2017/0281344 A1 | 10/2017 | Costello | |
| 2017/0281909 A1 | 10/2017 | Northrop et al. | |
| 2017/0281912 A1 | 10/2017 | Melder et al. | |
| 2017/0290593 A1 | 10/2017 | Cruise et al. | |
| 2017/0290654 A1 | 10/2017 | Sethna | |
| 2017/0296324 A1 | 10/2017 | Argentine | |
| 2017/0296325 A1 | 10/2017 | Marrocco et al. | |
| 2017/0303939 A1 | 10/2017 | Greenhalgh et al. | |
| 2017/0303942 A1 | 10/2017 | Greenhalgh et al. | |
| 2017/0303947 A1 | 10/2017 | Greenhalgh et al. | |
| 2017/0303948 A1 | 10/2017 | Wallace et al. | |
| 2017/0304041 A1 | 10/2017 | Argentine | |
| 2017/0304097 A1 | 10/2017 | Corwin et al. | |
| 2017/0304595 A1 | 10/2017 | Nagasrinivasa et al. | |
| 2017/0312109 A1 | 11/2017 | Le | |
| 2017/0312484 A1 | 11/2017 | Shipley et al. | |
| 2017/0316561 A1 | 11/2017 | Helm et al. | |
| 2017/0319826 A1 | 11/2017 | Bowman et al. | |
| 2017/0333228 A1 | 11/2017 | Orth et al. | |
| 2017/0333236 A1 | 11/2017 | Greenan | |
| 2017/0333678 A1 | 11/2017 | Bowman et al. | |
| 2017/0340383 A1 | 11/2017 | Bloom et al. | |
| 2017/0348014 A1 | 12/2017 | Wallace et al. | |
| 2017/0348514 A1 | 12/2017 | Guyon et al. | |
| 2017/0367712 A1 | 12/2017 | Johnson et al. | |
| 2018/0028779 A1 | 2/2018 | von Oepen et al. | |
| 2018/0036508 A1* | 2/2018 | Ozasa | A61M 25/0045 |
| 2018/0228493 A1* | 8/2018 | Aguilar | A61B 17/1214 |
| 2018/0250150 A1 | 9/2018 | Majercak et al. | |
| 2018/0280667 A1 | 10/2018 | Keren | |
| 2018/0325706 A1 | 11/2018 | Hebert et al. | |
| 2019/0159784 A1* | 5/2019 | Sananes | A61B 17/42 |
| 2019/0192162 A1* | 6/2019 | Lorenzo | A61B 17/12022 |
| 2019/0255290 A1 | 8/2019 | Snyder et al. | |
| 2019/0314033 A1* | 10/2019 | Mirigian | A61M 39/00 |
| 2019/0328398 A1 | 10/2019 | Lorenzo | |
| 2020/0138448 A1* | 5/2020 | Dasnurkar | A61B 17/00491 |
| 2020/0187951 A1* | 6/2020 | Blumenstyk | A61B 17/1214 |
| 2021/0001082 A1 | 1/2021 | Lorenzo et al. | |

FOREIGN PATENT DOCUMENTS

| | | |
|---|---|---|
| EP | 3092956 A1 | 11/2016 |
| EP | 3501427 A1 | 6/2019 |
| JP | 2006-334408 A | 12/2006 |
| JP | 2012-523943 A | 10/2012 |
| JP | 2013-78584 A | 5/2013 |
| WO | WO 2009/132045 A2 | 10/2009 |
| WO | WO 2012/158152 A1 | 11/2012 |
| WO | WO 2017/066386 A1 | 4/2017 |
| WO | WO 2018/022186 A1 | 2/2018 |

OTHER PUBLICATIONS

Extended European Search Report issued in corresponding European Patent Application No. 20 21 2970 dated May 28, 2021, pp. 1-7.

\* cited by examiner

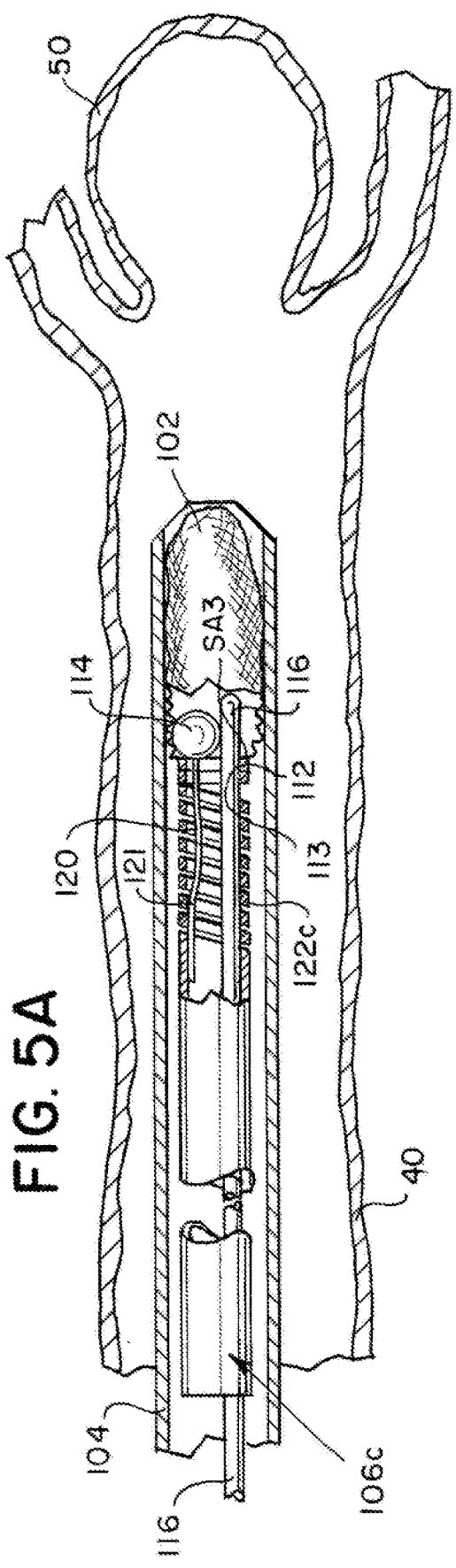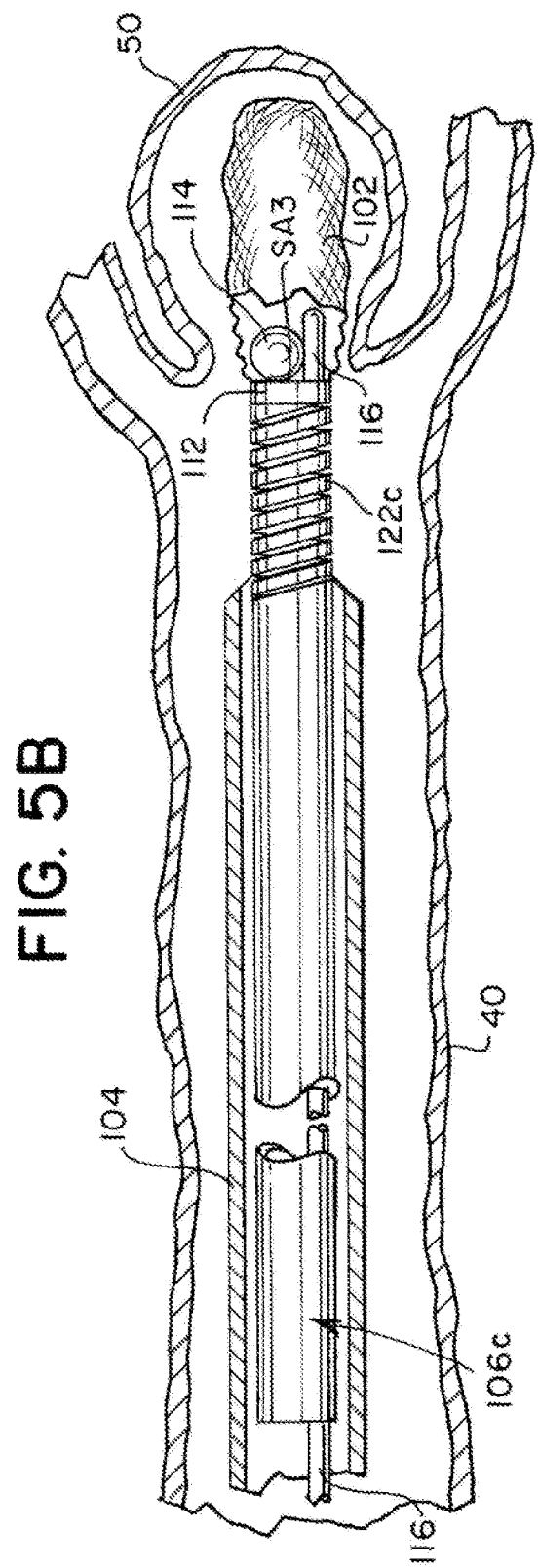

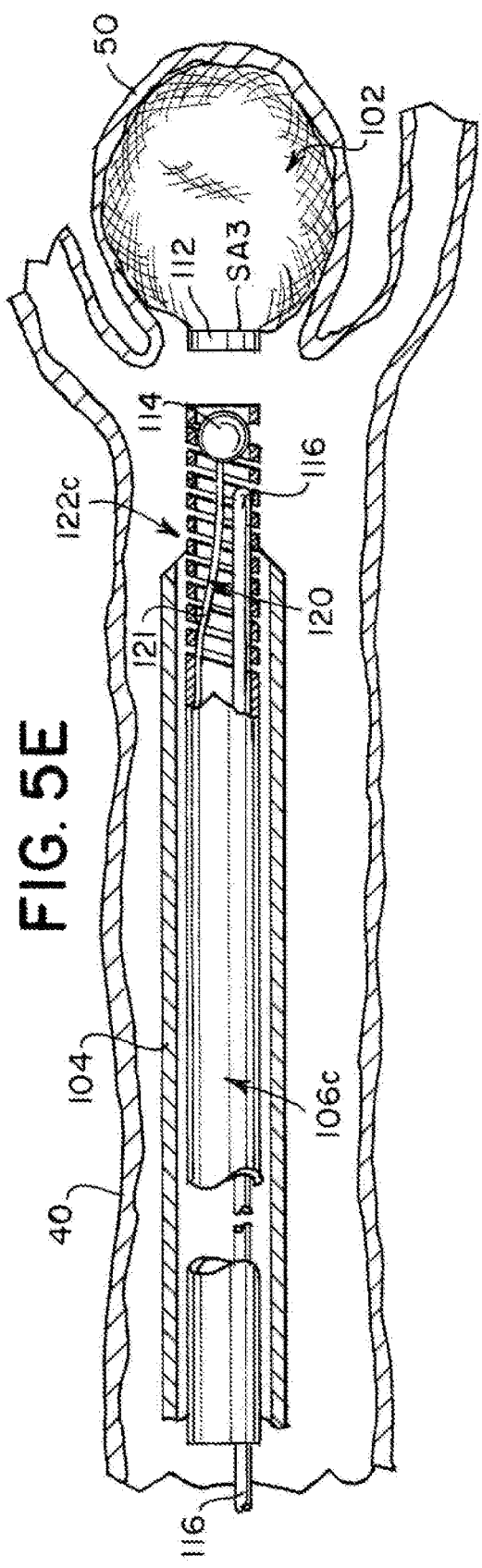
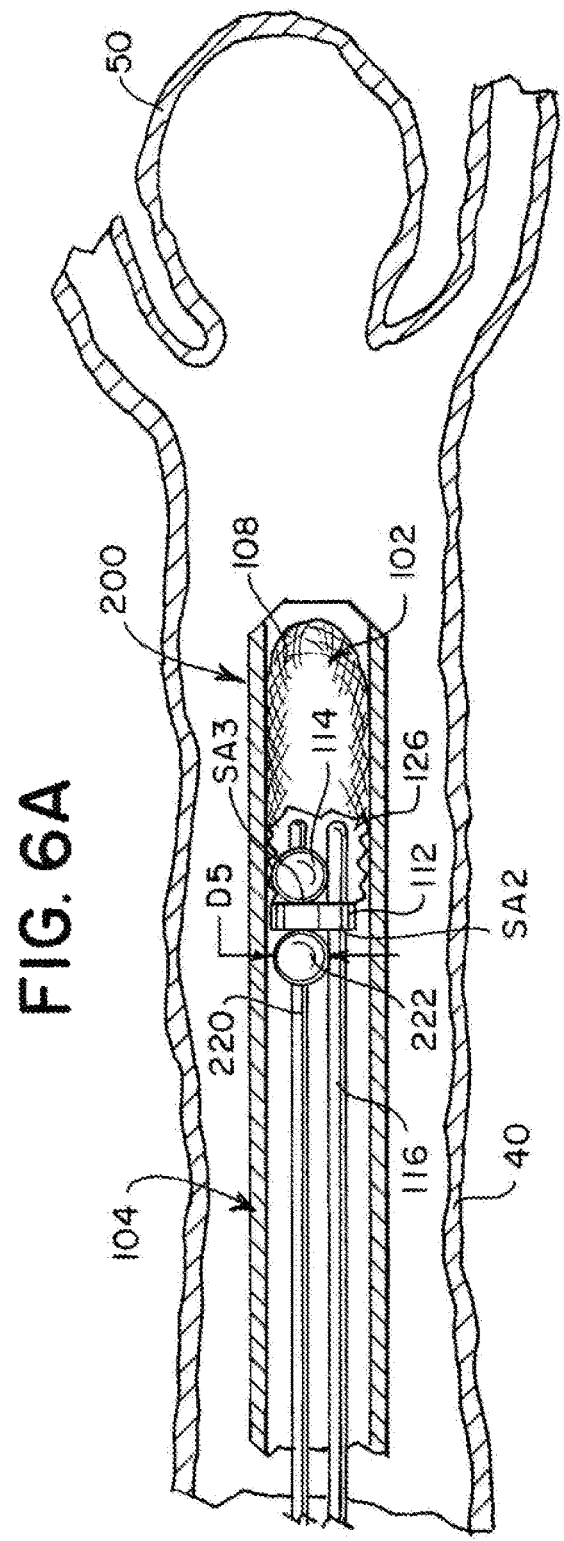

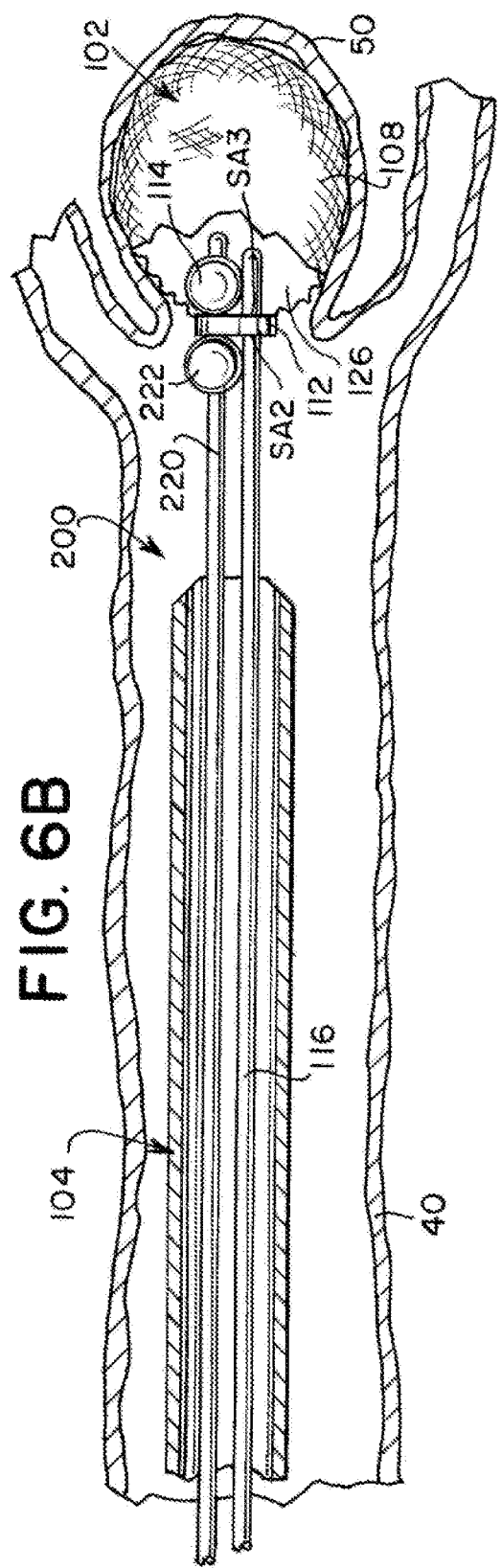
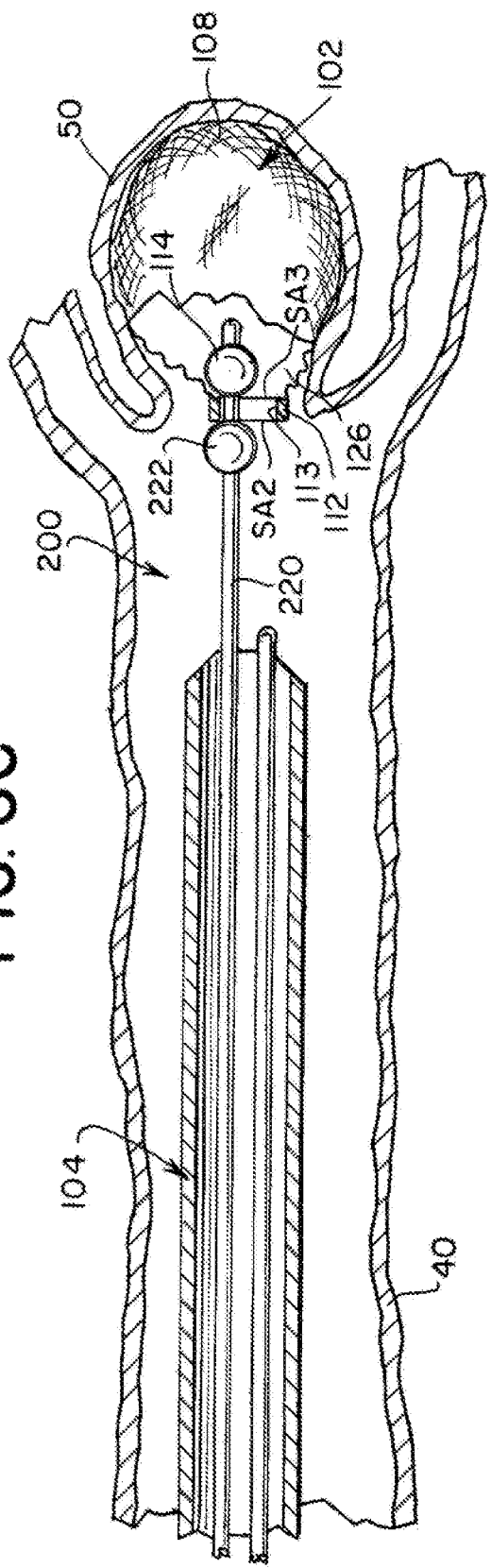

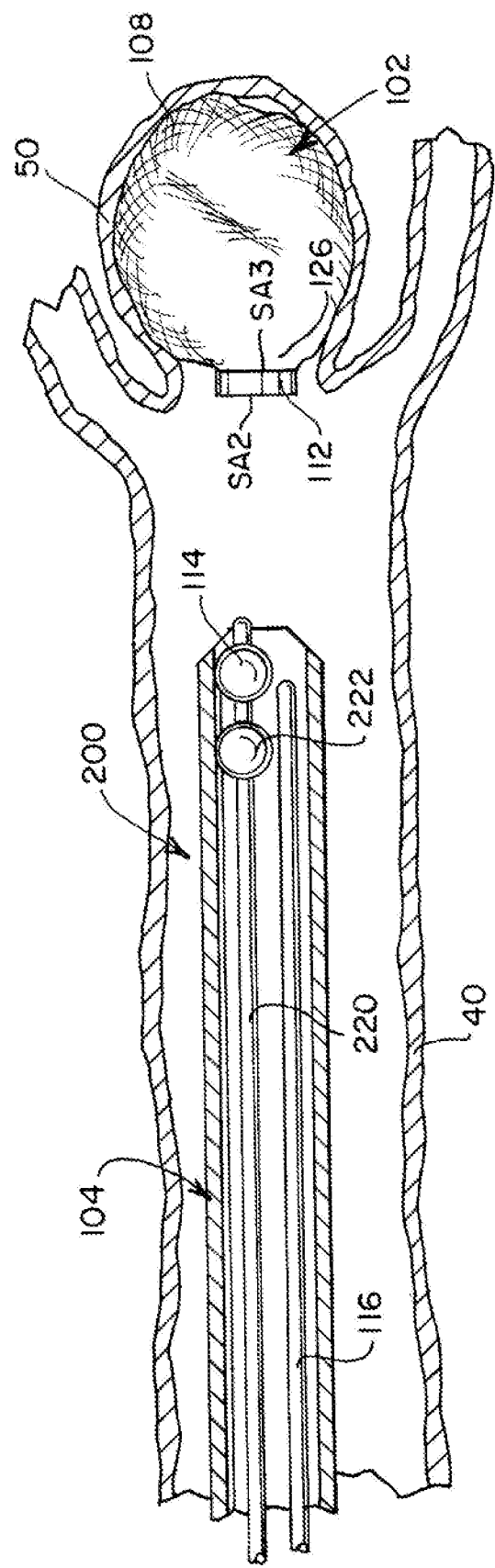

INTRAVASCULAR IMPLANT DEPLOYMENT SYSTEM

FIELD OF INVENTION

This invention generally relates to intravascular medical device systems that navigable through body vessels of a human subject. More particularly, this invention relates to delivery systems and delivery members for delivering and deploying an implantable medical device to a target location of a body vessel and methods of using the same.

BACKGROUND

The use of catheter delivery systems for positioning and deploying therapeutic devices, such as dilation balloons, stents, and embolic coils, in the vasculature of the human body has become a standard procedure for treating endovascular diseases. It has been found that such devices are particularly useful in treating areas where traditional operational procedures are impossible or pose a great risk to the patient, for example in the treatment of aneurysms in cranial blood vessels.

Procedures typically involve inserting a guide catheter (also referred to as a delivery catheter) into the vasculature of a patient and guiding it through the vasculature to a treatment site. A vascular occlusion device, such as an embolic coil or braid, can be attached to an implant engagement/deployment system (referred to herein equivalently as an "engagement system" or "deployment system") at a distal end a of a delivery member (e.g. micro-catheter) which pushes the vascular occlusion device through the guide catheter and out of the distal end of the guide catheter into the treatment site. Example delivery members and engagement/deployment systems are described in U.S. patent application Ser. No. 15/850,993 and U.S. patent application Ser. No. 15/964,857 each incorporated herein by reference.

Applicant recognizes a need for alternative methods, devices, and systems to provide an implant delivery member and implant engagement system for delivering and deploying vascular occlusion devices.

SUMMARY

An example system for deploying an intrasaccular implant to occlude an aneurysm can include the intrasaccular implant, a pusher tube, a securing wire, and a pull wire. The intrasaccular implant, pusher tube, securing wire, and pull wire can be sized to fit within a microcatheter.

The intrasaccular implant can include a securing ring thereon. The securing ring can include a proximal surface and an opening having an inner diameter. The opening of the securing ring can include a substantially circular shape defined by the inner diameter. The intrasaccular implant can include a braided mesh that is self-expandable upon exiting the microcatheter. The intrasaccular implant can include a cavity therein. The intrasaccular implant can include a substantially tubular braided mesh body. The body can include a first aperture oriented at a first region of the body and a second aperture oriented at a second region of the body. The securing ring can be disposed on the first region of the body approximate the first aperture. The second aperture can correspond to a free open end of the substantially tubular braided mesh body The pusher tube can include a distal surface sized to engage the proximal surface of the securing ring and positioned to face the proximal surface of the securing ring. A distal region of the pusher tube can be flexible. The distal region of the pusher tube that is flexible can include a flexibility array. The pusher tube can include a compressibly resilient portion at a distal region of the pusher tube.

The securing wire can extend through a lumen of the pusher tube and the opening of the securing ring. The securing wire can include an extended securing member thereon positioned on an opposite side of the securing ring in relation to the pusher tube. The securing member can include a securing member diameter measuring less than the inner diameter of the opening of the securing ring. The securing member can include a substantially spherical shape defined by the securing member diameter. The securing wire can be movable to pass the securing member through the opening in the securing ring when the pull wire has exited the opening of the securing ring. The securing wire can be coupled to an inner surface of the pusher tube by an attachment portion. The securing member can be disposed in the cavity of the implant.

The pull wire can extend through the lumen of the pusher tube and the opening of the securing ring. The pull wire can include a pull wire diameter such that the sum of the securing member diameter and the pull wire diameter measures greater than the inner diameter of the opening of the securing ring. The pull wire can include a substantially circularly shaped perimeter defined by the pull wire diameter. The pull wire can be movable to exit the opening of the securing ring while the securing wire is extended through the ring. A portion of the pull wire can be disposed in the cavity of the implant.

If the pusher tube includes a compressibly resilient portion, the securing wire can hold the compressibly resilient portion in compression. The securing member of the securing wire can be engaged to the securing ring, and an elongated portion of the securing wire can be affixed to the pusher tube in a proximal direction in relation to the compressibly resilient portion. Tension in the portion of the securing member extending from a coupling of the securing wire to the inner surface of the pusher tube to the engagement of the securing member to the securing ring can hold the compressibly resilient distal region in compression. The compressibly resilient distal region can be configured to expand and push the securing ring over the securing member when the pull wire has exited the securing ring.

An example method for deploying an intrasaccular implant in an aneurysm can include one or more of the following steps presented in no particular order. The example method can include additional steps as would be appreciated and understood by a person of ordinary skill in the art. The example method can be performed using an example system as disclosed herein, a variation thereof, or an alternative thereto as would be appreciated and understood by a person of ordinary skill in the art. A system including a microcatheter, a pusher tube, a securing wire a pull wire, and an intrasaccular implant can be selected. The system can be selected such that the securing wire includes a radially extending securing member and the implant includes a securing ring.

The system can be positioned in a delivery configuration such that pusher tube, securing wire, pull wire, and implant are positioned within the microcatheter, the pusher tube is in the proximal direction in relation to the securing ring, the securing wire extends through the securing ring and pusher tube such that the securing member is positioned in the distal direction from the securing ring, and the pull wire extends through the pusher tube and the securing ring.

The implant can be moved in the distal direction through the microcatheter by moving the pusher tube, pull wire, and securing wire in the distal direction.

The intrasaccular implant can be extended into a sac of the aneurysm. The step of extending the intrasaccular implant into the sac of the aneurysm further can include allowing the implant to self-expand in the sac.

The pull wire can be retracted in the proximal direction to free the pull wire from the securing ring. Retracting the securing wire from the securing ring further can include retracting the pusher tube in the proximal direction while the securing wire is coupled to the pusher tube. The securing wire can be retracted from the securing ring by moving the securing member through the securing ring when the pull wire is free from the securing ring.

Attachment of the implant to the pusher tube can be maintained by engaging the securing member to a distal surface of the engagement ring while engaging a distal surface of the pusher tube to a proximal surface of the engagement ring. Maintaining attachment of the implant to the pusher tube further can include inhibiting the securing member from passing through the securing ring by maintaining the pull wire to extend within the securing ring.

An example system for treating an aneurysm can include a microcatheter, a pusher tube, an intrasaccular implant, a securing wire, and a pull wire.

The intrasaccular implant can include a securing ring. The securing ring can have an inner diameter.

The pusher tube can be oriented within the microcatheter. The pusher tube can include a compressibly resilient distal region and an inner surface. The pusher tube can include distal surface at the distal region of the pusher tube, sized to engage a proximal surface of the securing ring.

The securing wire can include an extended securing member and an attachment portion. The securing member can include a securing member diameter measuring less than the inner diameter of the securing ring. The securing member can be positioned in the distal direction in relation to the securing ring. The attachment portion of the securing wire can be coupled to the inner surface of the pusher tube in the proximal direction in relation to the compressibly resilient distal region of the pusher tube. The securing member of the securing wire can be engaged to the securing ring.

The pull wire can be oriented in the pusher tube, extend through the securing ring. The pull wire can include a pull wire dimension less than the inner diameter of the securing ring. The sum of the securing member diameter and the pull wire diameter can be greater than the inner diameter of the securing ring.

The pull wire can be movable to exit the securing ring while the securing wire is extending through the securing ring. The compressibly resilient distal region of the pusher tube can be compressed due to tension in the securing wire over a portion of the securing wire extending from the securing ring to the coupling of the attachment portion to the inner surface of the pusher tube. The compressibly resilient distal region can be configured to expand and push the securing ring over the securing member when the pull wire has exited the securing ring.

Another example intravascular treatment system can include an implant, a pull wire, and a securing wire.

The implant can include an embolic body and a securing ring affixed to the body. The securing ring can include a proximal surface, a distal surface, and an opening including an inner diameter.

The pull wire having a pull wire diameter can extend through the opening of the securing ring. The pull wire can be translatable in the proximal direction to exit the opening in the securing ring.

The securing wire can extend through the opening of the securing ring. The securing wire can have an extended securing member thereon and an extended pusher member thereon. The securing member can be positioned in the distal direction in relation to the distal surface of the securing ring. The pusher member can be positioned in the proximal direction in relation to the proximal surface of the securing ring. The securing member can have a diameter dimensioned such that the sum of the pull wire diameter and securing member diameter is greater than the inner diameter of the securing ring. The pushing member can have a diameter dimensioned such that the sum of the pull wire diameter and the pushing member diameter is greater than the inner diameter of the securing member. The securing member can be movable to engage the distal surface of the securing ring when the securing wire is pulled proximally. The pusher member can be movable to engage the proximal surface of the securing ring when the securing wire is pushed distally. The securing member and pusher member are each inhibited from moving through the opening in the securing ring due to the extension of the pull wire through the securing ring. The securing wire can be translatable in the proximal direction to exit the opening in the securing ring when the pull wire is absent from the opening.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIGS. 5A through 5E are a sequence of illustrations during a treatment of an intravascular implant system having a compressibly resilient distal region according to aspects of the present invention; and FIGS. 6A through 6D are a sequence of illustrations during a treatment of an intravascular implant system lacking a pusher tube.

DETAILED DESCRIPTION

Figure 1A:
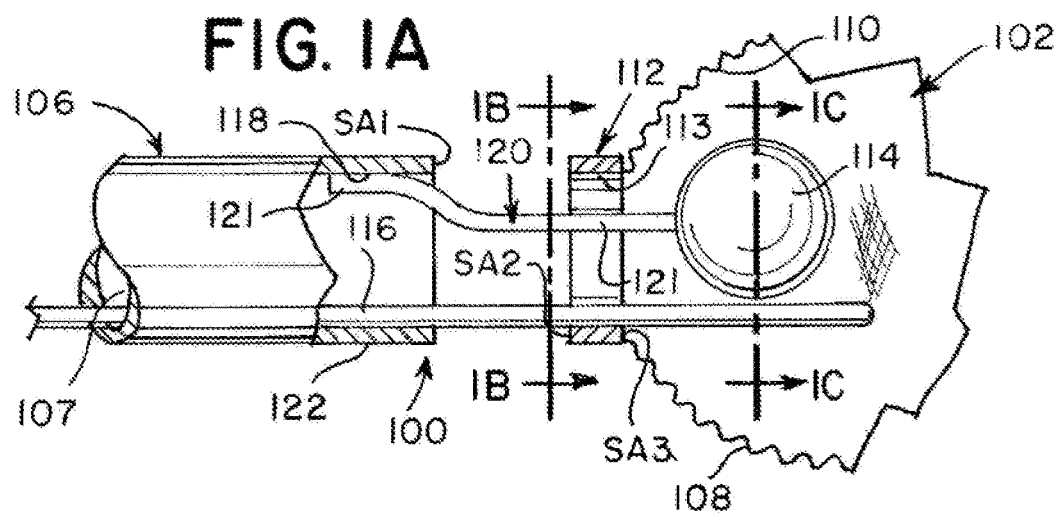
FIG. 1A is an illustration of an example intravascular implant system according to aspects of the present invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

As used herein, the terms "tubular" and "tube" are not limited to a structure that is a right cylinder or strictly circumferential in cross-section or of a uniform cross-section throughout its length. For example, the tubular structure or system is generally illustrated as a substantially right cylindrical structure. However, the tubular system may have a tapered outer surface, a curved outer surface, and/or a partially flat outer surface without departing from the scope of the present disclosure.

As used herein, the term "wire" includes solid core and hollow elongated tubular structures.

A system is disclosed herein that can be used to push, track, deploy, position, and detach an implant at an aneurysm. The system can include an engagement/deployment system and an embolic implant. The embolic implant can be a braid that is mechanically attached to the engagement/deployment system, pushed by a delivery pusher (e.g. hypotube) of the engagement/deployment system to a treatment site using a microcatheter, wherein the microcatheter is pre-placed at the level of the aneurysm neck and is used to track the device to the treatment site/lesion. The delivery pusher extends from the proximal to the distal end of the delivery microcatheter such that a physician can manipulate a proximal end of the delivery pusher to push the distal end of the delivery pusher out of the distal end of the microcatheter.

The engagement/deployment system includes a two wire securing system to secure the implant to the distal end of the hypotube (delivery pusher). One of the wires can have a bump, extension, or other such securing feature thereon (referred to herein as an "securing wire") and the other can have a substantially uniform circumference (referred to herein as a "pull wire"). The pull wire can be elongated to extend out of the patient or otherwise be available for manipulation during treatment such that the pull wire can be pulled proximally in relation to the securing wire.

The delivery pusher can include a hypotube (metal or polymer) having with a flexible distal portion. Flexibility of the distal portion of the hypotube can be attained by cutting a spiral or an interrupted cut through the wall of the hypotube. Additionally, or alternatively, the pusher can include an extended pushing member formed on the securing wire in a proximal direction in relation to the securing member on the securing wire. In examples where the pusher includes a hypotube, the securing wire can be tethered to the pusher tube. In examples where the pusher lacks a hypotube and includes a securing member on the securing wire, the securing wire can have an elongated portion that can be pulled proximally independent of the pull wire.

The intrasaccular implant can have an annular ring attached to its proximal end to connect the engagement/deployment system to the implant. To attach the implant to the engagement/deployment system, the securing feature of the securing wire is inserted into the annular ring of the implant first, then the pull wire is inserted into the annular ring of the implant. This secures the implant to the pusher as the inner diameter of the annular ring is smaller than the diameter of the pull wire plus the diameter of the securing feature.

To deploy the implant the pull wire can be retracted, thereby enabling the securing feature to separate from the implant as the diameter of the securing feature is smaller than the inner diameter of the annular ring. Once the pull wire is retracted the pusher tube can be retracted separating the implant from the engagement/deployment system.

FIG. 1A is an illustration of an example intravascular implant system 100 including an implant 102, pusher tube 106, pull wire 116, and securing wire 120. The implant 102 includes a body 108 that can be an embolic braid, coil, or other such intravascular occlusion device. The body 108 can include a braid that is sized, shaped, and otherwise configured for implantation in an aneurysm. Alternatively, the body 108 can be configured to occlude blood vessels or vascular openings.

The implant 102 includes a securing ring 112 having a proximal surface SA2, a distal surface SA3, and an opening 113. The pusher tube 106 can have a lumen 107 therethrough and a distal surface SA1 sized to engage the proximal surface SA2 of the securing ring 112. The distal surface SA1 of the pusher tube 106 can be positioned to face the proximal surface SA2 of the securing ring 112. The securing wire 120 includes a securing member 114 thereon. When the implant 102 is attached to the pusher tube 106, the securing wire 120 and the pull wire 116 each extend through the lumen 107 of the pusher tube 106 and the opening 113 of the securing ring 112, and the securing member 114 is positioned on the opposite side of the securing ring 112 in relation to the pusher tube 106. The pull wire 120 and securing member 114 can be sized such that when placed side-by-side the securing member is inhibited from passing through an opening of the securing ring 112. The body 108 of the implant 102 can include a cavity 110 that is sized such that the securing member 114 and a distal portion of the pull wire 116 can fit therein when the implant 102 is secured to the pusher tube 106.

Figure 1B:
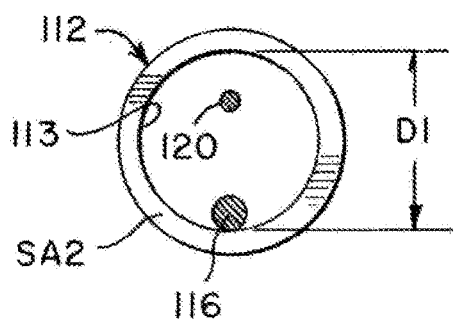
FIGS. 1B and 1C are cross-sectional view illustrations of the example intravascular implant system as indicated in FIG. 1A.

FIG. 1B is a cross-sectional view of the system 100 bisecting the securing wire 120 and pull wire 116 and looking in the distal direction as indicated in FIG. 1A. The opening 113 of the securing ring 112 can be substantially circular, having an inner diameter D1.

Figure 1C:
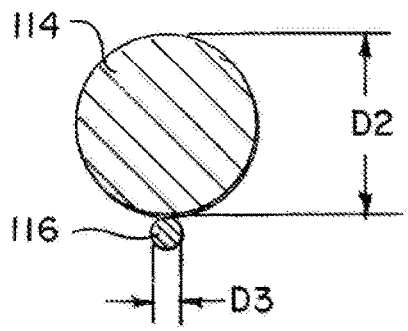

FIG. 1C is a cross-sectional view of the system 100 bisecting the securing member 114 and the pull wire 116 and looking in the distal direction as indicated in FIG. 1A. The pull wire 116 can have a substantially circular cross section and perimeter having a diameter D3. The securing member 114 can have a circular cross section having a diameter D2. The securing member 114 can further have a substantially spherical shape defined by the circular cross section diameter D2. Alternatively, the securing member can be longer or shorter along the axis of the securing member 114 while maintaining the circular cross section diameter D2.

Referring collectively to FIGS. 1A through 1C, the sum of the pull wire diameter D3 and the securing member diameter D2 can be greater than the inner diameter D1 of the securing ring 112 to thereby inhibit the securing member 114 from passing through the securing ring 112 when the pull wire 116 is extended through the securing ring 112. The pull wire can be pulled proximally to exit the opening of the securing ring 112. The securing wire 120 is movable to pass the securing member 114 through the opening 113 in the securing ring 112 when the pull wire 116 has exited the opening of the securing ring. As illustrated, the securing wire 120 is coupled to an inner surface of the pusher tube by an attachment portion of the securing wire 120.

The securing wire 120 can include an elongated portion 121 extending through the securing ring 112. The elongated portion 121 of the securing wire 120 is smaller in diameter than the securing member 114 such that the securing member 114 extends radially outwardly from the elongated portion 121. The elongated portion 121 can be sufficiently small in diameter to allow the securing wire 120 and pull wire 116 to both be positioned to extend through the opening 113 of the securing ring 112.

The pusher can include an elongated hypotube 106. The hypotube can extend through vasculature 40 of a patient such that the hypotube 106 can be manipulated at its proximal end to position the implant 102 at a treatment site during treatment. The distal surface SA1 of the pusher 106 can be sized to engage the proximal surface SA2 of the securing ring 112 and positioned to face the proximal surface SA2 of the implant 102. The pull wire 116 can extend through the lumen of the hypotube 106 and can be manipulated at the proximal end of the hypotube to move the distal end of the pull wire 116 proximally in relation to the distal portion 122 of the hypotube 106.

FIGS. 2A through 2H are a sequence of illustrations of the intravascular implant system 100 during a treatment.

Figure 2A:
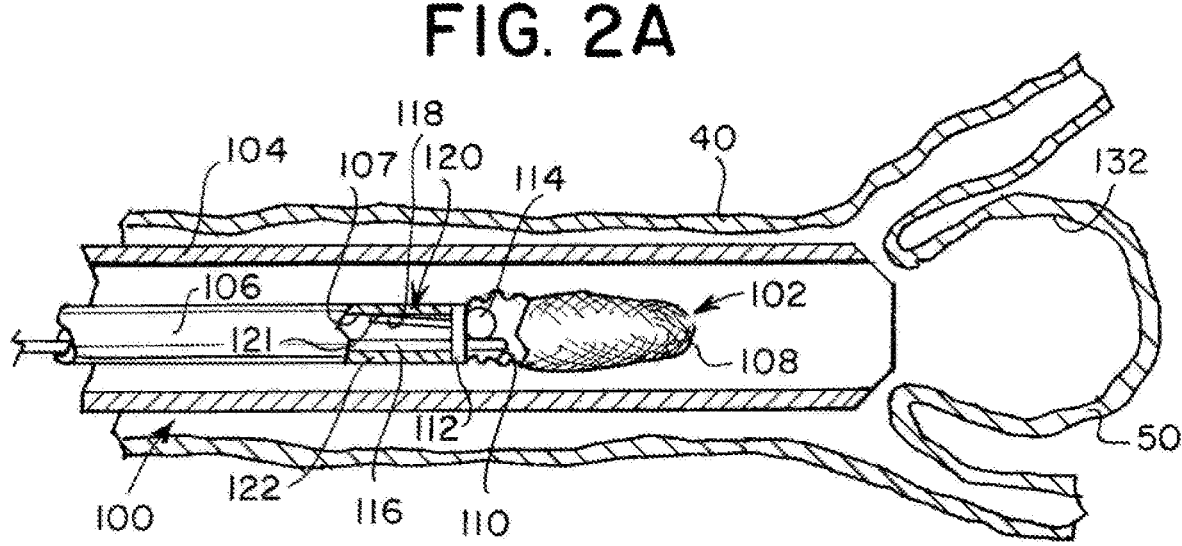
FIGS. 2A through 2H are a sequence of illustrations of the intravascular implant system during a treatment according to aspects of the present invention.

FIG. 2A illustrates the implant 102 being pushed distally through a microcatheter 104 by a pusher tube 106. The implant 102, pusher tube 106, securing wire 120, and pull wire 116 are sized to fit within the microcatheter 104. As illustrated, the implant 100 is detachably attached to the pusher tube 106. A securing wire 120 and pull wire 116 are extended through a lumen 107 of the pusher tube 106 and through an opening 113 of a securing ring 112 affixed to the implant 102. Positioned as such, the securing wire 120, pull wire 116, and securing ring 112 maintain the attachment between the implant 102 and the pusher tube 106 as the implant 102 is translated through the microcatheter 104. The securing member 114 is inhibited from passing through the opening 113 of the securing ring 112 by virtue of the position of the pull wire 116 extending through the opening 113. As illustrated, the elongated portion 121 of the securing wire 120 can be affixed to the pusher tube 106. Alternatively, the elongated portion 121 can extend through the pusher tube 106, positioned for manipulation near a proximal end of the system (e.g. outside of a patient). If the securing wire 120 is affixed to the pusher tube 106, preferably, the securing wire 120 is affixed to an inner surface 118 within the pusher tube lumen 107. Alternatively, the securing wire 120 can be affixed to an outer surface or distal face of the pusher tube 106; however such position might expose the securing wire 120 to potential damage during delivery or handling. As illustrated, the body 108 of the implant 100 includes a braided mesh that is self-expandable upon exiting the microcatheter 104.

Figure 2B:
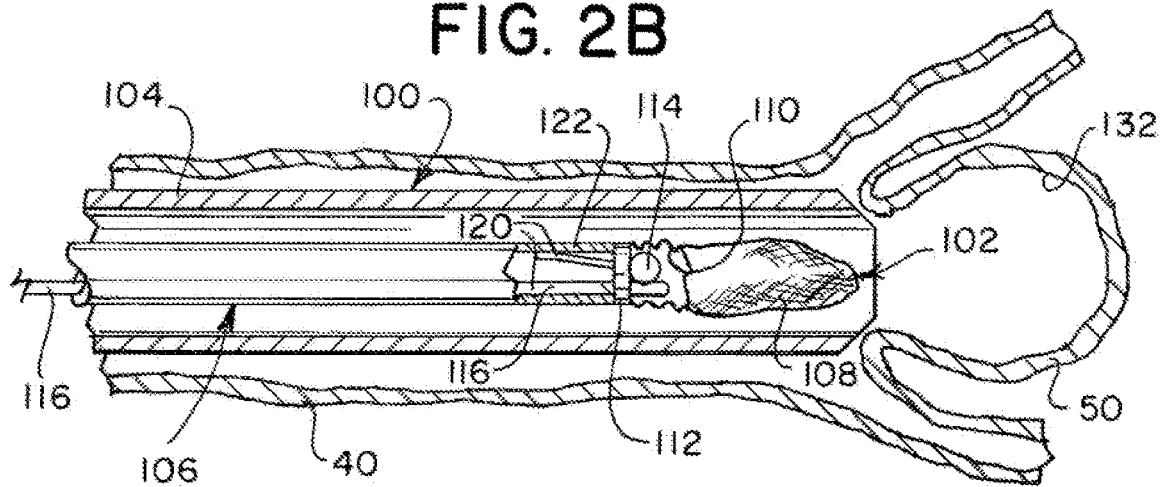

FIG. 2B illustrates the implant 102 being pushed further distally through the microcatheter 104 while remaining detachably attached to the pusher tube 106. The pull wire 116 is maintained in position through the opening 113.

Figure 2C:
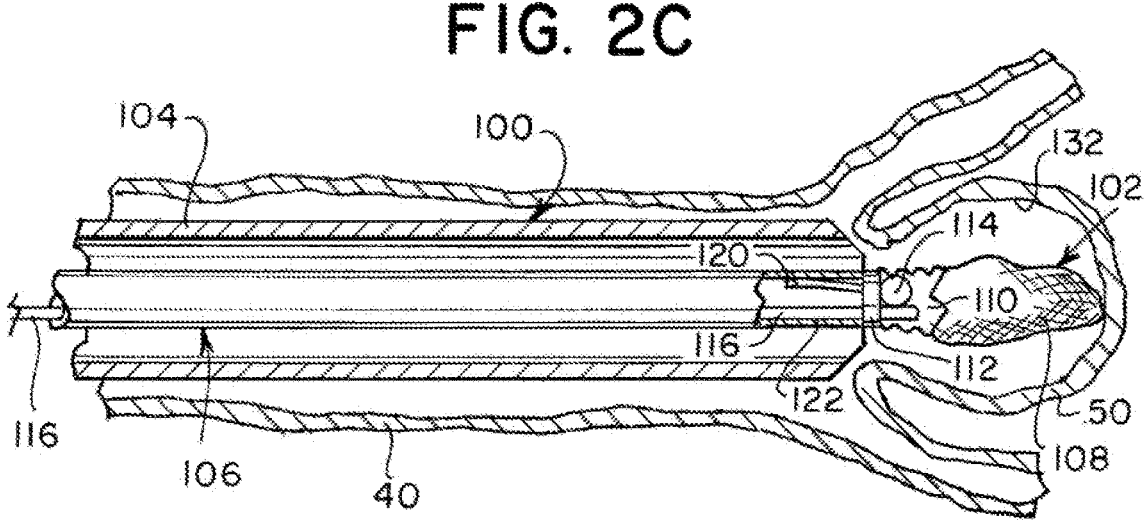

FIG. 2C illustrates the implant 102 pushed distally by the pusher tube 106 from a distal end of the microcatheter 104 into an aneurysm 50. The implant 102 remains detachably attached to the pusher tube 106 by virtue of the pull wire 116 and securing wire 120 extending through the opening 113 of the securing ring 112.

Figure 2D:
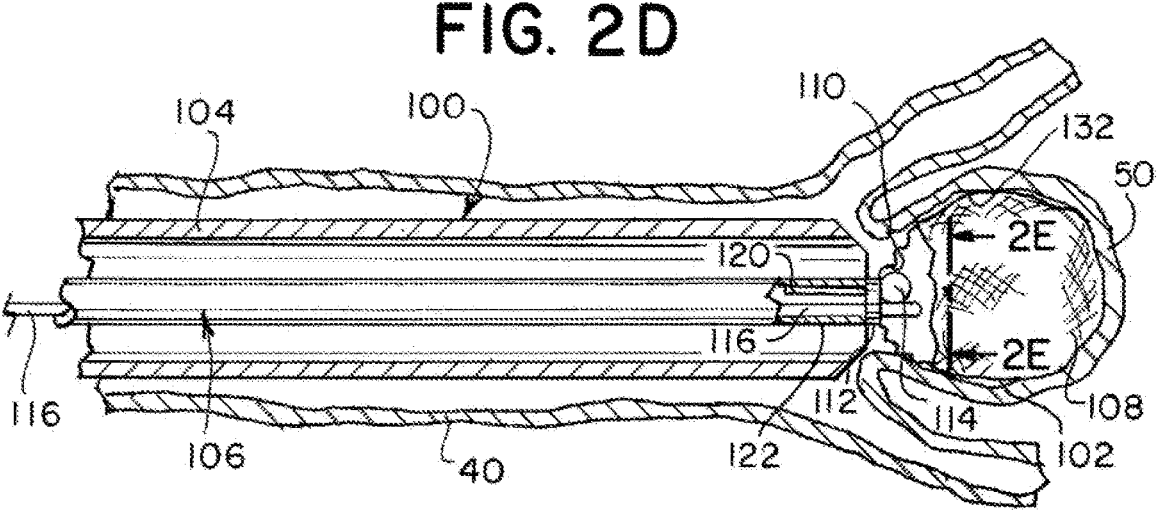

FIG. 2D illustrates the implant 102 expanding with the sac 132 of the aneurysm 50 while remaining detachably attached to the pusher tube 106. The implant can include an embolic braid that expands to contact aneurysm walls as illustrated, an embolic braid that forms an alternative shape, an embolic coil that winds within the aneurysm, and/or other suitable material for an occlusion device. FIG. 2D represents the implant 102 in a final implanted position immediately prior to detachment of the implant 102 from the pusher tube 106. At this step and all steps prior, the implant 102 can be retracted or otherwise repositioned by virtue of the implant's attachment to the pusher tube 106. At this and prior steps, attachment of the implant 102 to the pusher tube 106c is maintained by inhibiting the securing member 114 from passing through the securing ring 112 by maintaining the pull wire 116 to extend within the securing ring 112.

Figure 2E:
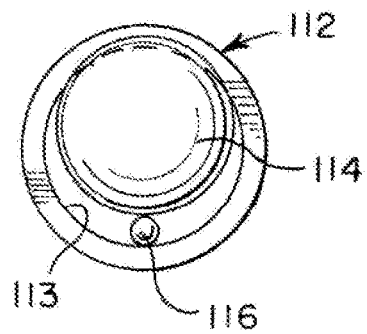

FIG. 2E illustrates a view of the system 100 at a position distal to the system 100 and looking in the proximal direction as indicated in FIG. 2D. The securing member 114 is illustrated as overlapping the securing ring 112. The overlap of the securing member 114 and the securing ring 112 inhibits the securing member 114 from passing through the opening 113 of the securing ring 112.

Figure 2G:
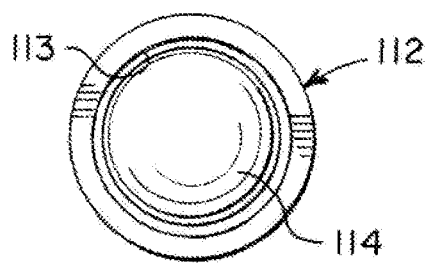
Figure 2F:
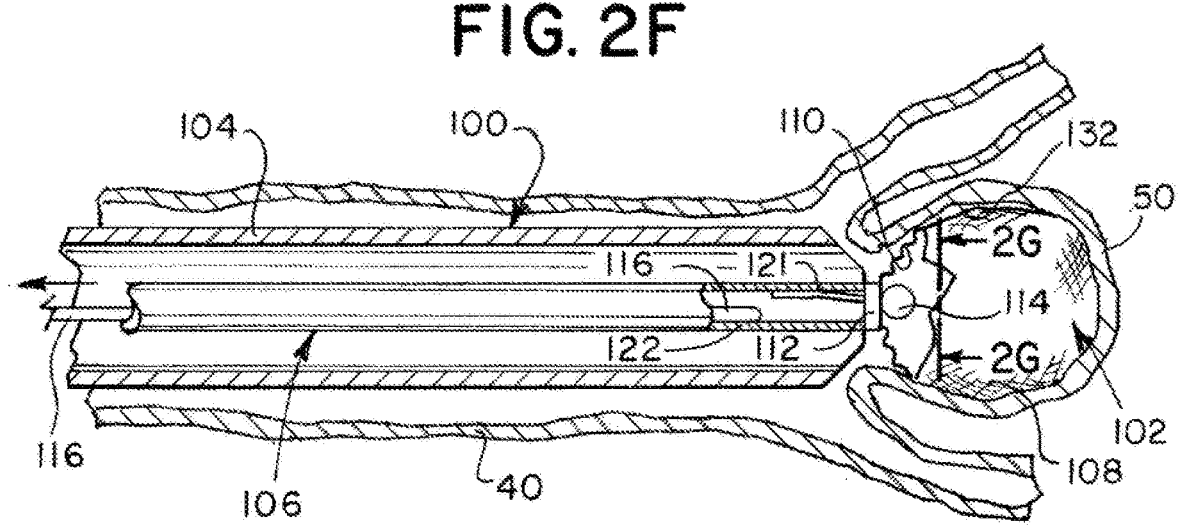

FIG. 2F illustrates an initial step for detaching the implant 102 from the pusher tube 106. The pull wire 116 can be configured such that a user can pull a distal portion of the pull wire in a proximal direction in relation to a distal portion 122 of the pusher tube 106. The pull wire 116 can be manipulated similar to pull wires in mechanical engagement/deployment systems as known to a person of ordinary skill in the art. Immediately after the pull wire is retracted, the securing member 114 can begin to move through the opening 113 of the securing ring 112, particularly if the elongated portion 121 of the securing wire 120 is under tension. Alternatively, the securing wire 120 can remain extended through the opening 113 of the securing ring 112 until the system 100 is further manipulated.

FIG. 2G illustrates a view of the system 100 at a position distal to the system 100 and looking in the proximal direction as indicated in FIG. 2F. The securing member 114 is illustrated as positioned centrally within the opening 113 of the securing ring 112. The removal of the pull wire 116 allows the securing member 114 to move so that it no longer overlaps the securing ring 112. FIG. 2G illustrates that the securing member 114 is sized to move through the opening 113 of the securing ring 112 when the opening 113 of the securing ring is unobstructed by the pull wire 116 (or other obstruction).

Figure 2H:
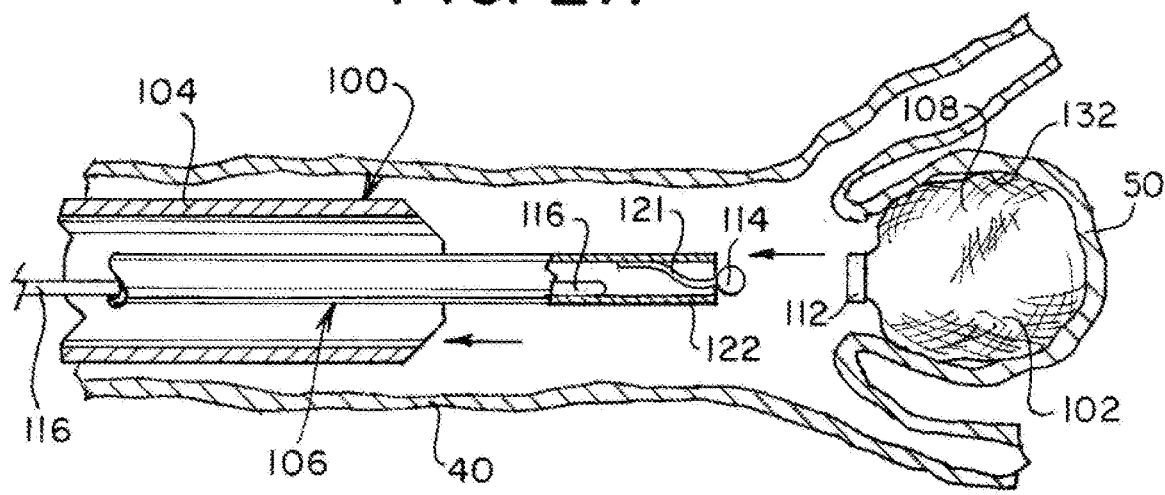

FIG. 2H illustrates the pusher tube 106 and securing wire 120 retracted from the implant 102. Once the pull wire 116 is retracted from the opening 113 in the securing ring 112 of the implant 102, the securing member 114 is able to move through the opening 113. As illustrated, the securing wire 120 is affixed to the pusher tube 106 by an attachment portion 121 and is therefore retracted by virtue of the pusher tube 106 being retracted. Alternatively, the securing wire 120 need not be affixed to the pusher tube 106, and in such cases the securing wire 120 can be configured to be retracted independent of the pusher tube 106. In either alternative, optionally, the distal portion 122 of the pusher tube 106 can elongated to cause the distal end of the pusher tube 106 to move distally toward the securing member 114, thereby pushing the securing ring 112 over the securing member 114.

Once detached, the implant 102 can be difficult to retract or otherwise reposition compared to the ease with which the implant 102 can be retracted and repositioned prior to detachment. The pusher tube 106, pull wire 116, and securing wire 120 can be retracted through the microcatheter 104. The microcatheter 104 can remain in place to provide a conduit for delivery of additional treatment devices, or the microcatheter 104 can be retracted together with the pusher tube 106, pull wire 116, and securing wire 120.

Figure 3A:
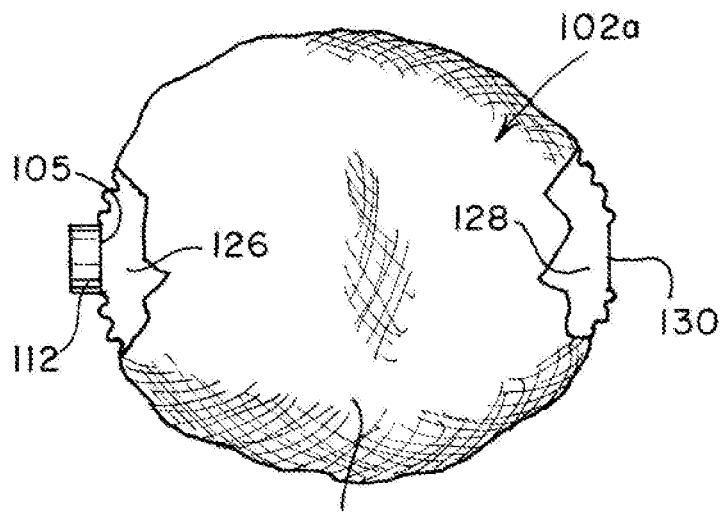
FIG. 3A is an illustration of an example implant according to aspects of the present invention.

FIG. 3A is an illustration of an example implant 102a including a substantially tubular braided mesh body 108a. The body 108a as illustrated includes a first aperture 105 and a second aperture 130 at either ends of the tube 108a. The first aperture 105 can be oriented at a first region 126 of the body 108a. The securing ring 112 can be positioned on the first region 126 of the body. The second aperture 130 can be oriented on a second region 128 of the body 108a. The securing ring 112 can be attached to the body 108a at the first aperture 105. The second aperture can be a free open end of the body 108a.

The first region 126 represents the region closest to the engagement/deployment system when the implant 102a is positioned within the aneurysm 50. If portions of the implant 102a are retracted into the microcatheter 104 for redeployment, the first region 126 enters the microcatheter before the second region 128.

Figure 3B:
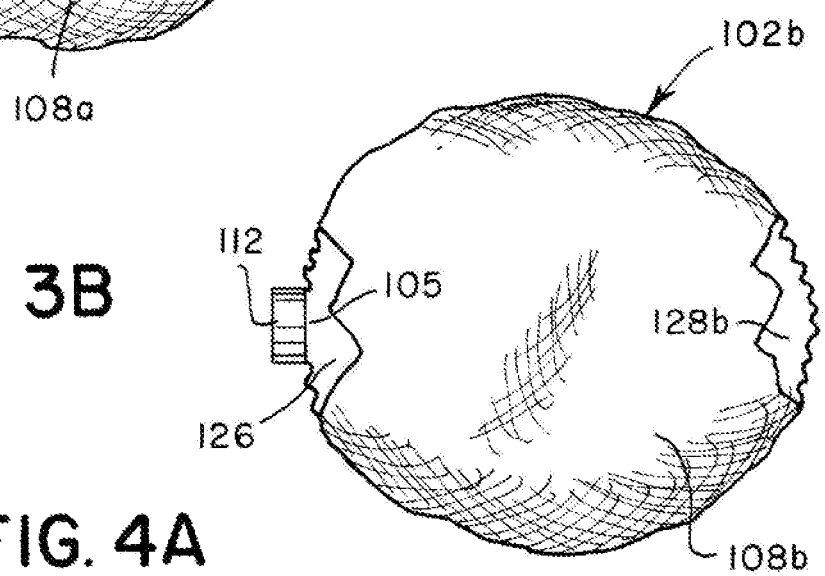
FIG. 3B is an illustration of another example implant according to aspects of the present invention.

FIG. 3B is an illustration of another example implant 102b including a braided sack body 108b having an aperture 105 on a first region 126 with the securing ring 112 affixed at the aperture 105 similar to the first aperture 105 of the implant 102a illustrated FIG. 3A. The implant 102b illustrated in FIG. 3B lacks a second aperture 130 on its second region 128b.

Figure 4A:
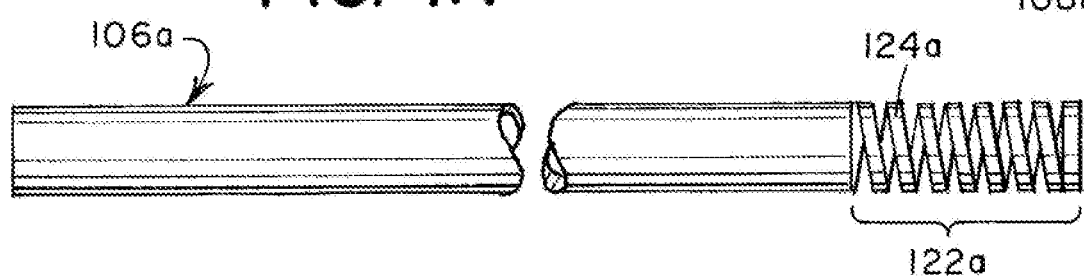
FIG. 4A is an illustration of an example flexible portion of a pusher tube according to aspects of the present invention.

FIG. 4A is an illustration of an example flexible distal portion 122a of a pusher tube 106a. The flexible distal portion 122a can include a flexibility array 124a that includes a helical cut.

Figure 4B:
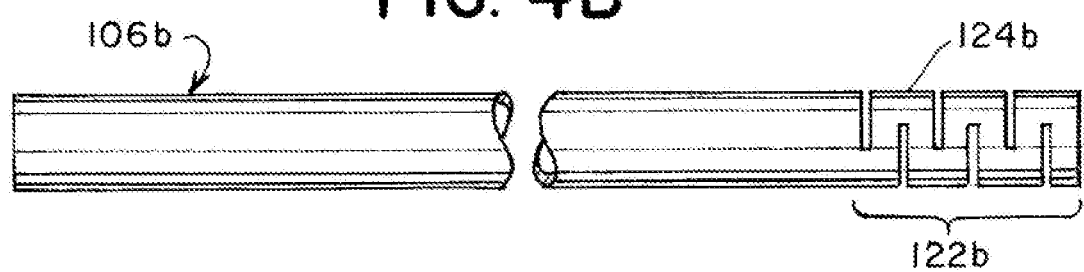
FIG. 4B is an illustration of another example flexible portion of a pusher tube according to aspects of the present invention.

FIG. 4B is an illustration of another example flexible distal portion 122b of a pusher tube 106b. The flexible distal portion 122b can include a flexibility array 124b that includes arcuate circumferential interference cuts.

FIGS. 5A through 5E are a sequence of illustrations during a treatment of an intravascular implant system having a pusher tube 106c having a compressibly resilient distal region 122c.

FIG. 5A is an illustration of the implant 102 being pushed distally by the pusher tube 106c. Similar to as illustrated and described in relation to FIG. 1 and FIG. 2A, the implant 102 is detachably attached to the pusher tube 106c by virtue of the securing wire 120 and pull wire 116 extending through the opening 113 in the securing ring 112 of the implant 102. As illustrated in FIG. 5A, the distal region 122c is compressed. The distal region 122c is held in compression due to tension on the elongated, attachment portion 121 of the securing wire 120. The attachment portion 121 under tension extends from the securing ring 112 to a coupling of the portion 121 to the inner surface 118 of the pusher tube 106. The securing member 114 is inhibited from moving through the securing ring 112 by virtue of the pull wire 116 extending through the securing ring 112 and the relative diameters D1, D2, D3 of the securing ring opening 113, securing member 114 and pull wire 116. The securing member 114 presses against a distal surface SA3 of the securing ring 112 while the attachment portion 121 of the securing wire 120 is attached to the pusher tube 106c in a proximal direction in relation to the compressed region 122c.

The tube 106c can further include a flexible region 122a, 122b as illustrated in FIGS. 4A and 4B. In such examples, the flexible region 122a, 122b is preferably positioned in a proximal direction in relation to the compressed region 122c.

FIG. 5B illustrates the implant 102 being positioned in an aneurysm 50 while remaining attached to the pusher tube 106c. The compressed region 122c remains compressed. The implant 102 can self-expand in the sac of the aneurysm 50.

Figure 5C:
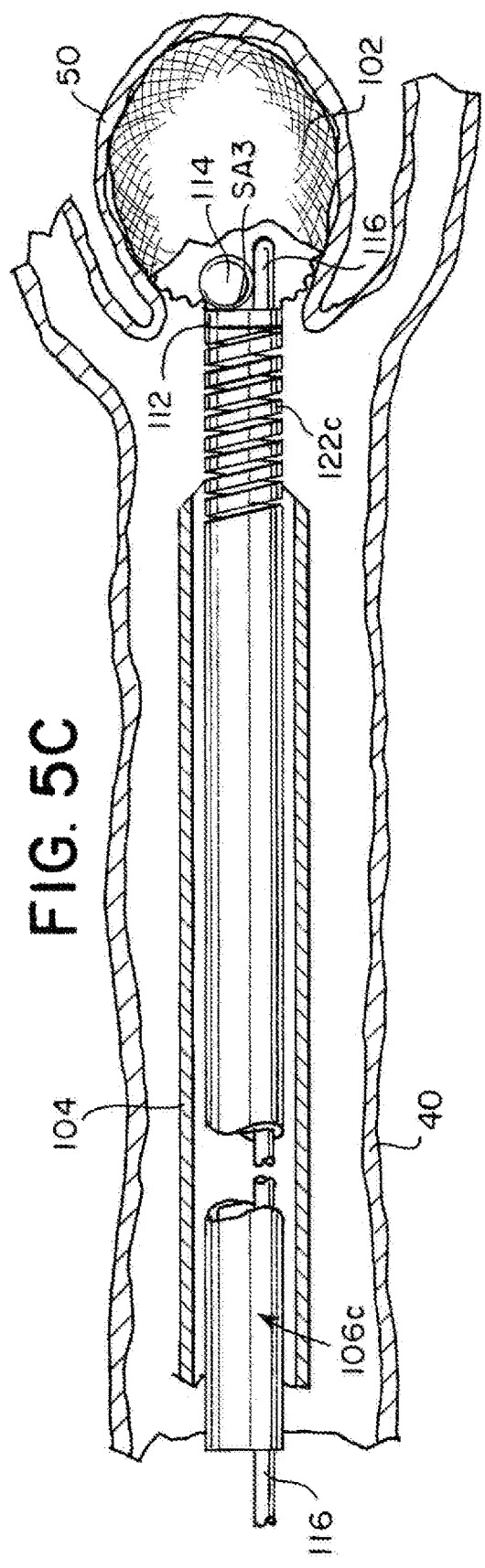

FIG. 5C illustrates the implant 102 expanded to a final implanted position within the aneurysm 50. The implant 102 remains attached to the pusher tube 106c while the compressed region 122c remains compressed. At this and prior steps, the implant 102 can be retracted proximally by retracting the pusher tube 106c proximally. At this and prior steps, attachment of the implant 102 to the pusher tube 106c is maintained by inhibiting the securing member 114 from passing through the securing ring 112 by maintaining the pull wire 116 to extend within the securing ring 112.

Figure 5D:
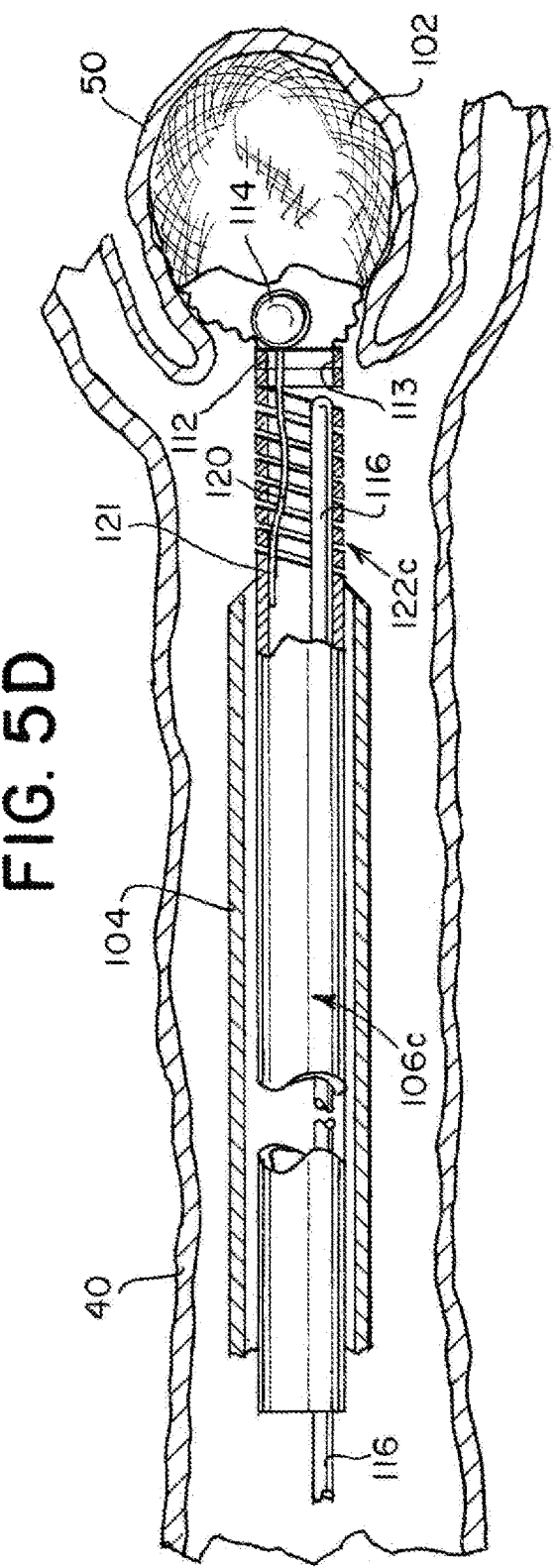

FIG. 5D is an illustration of the instant the pull wire 116 is retracted to exit the securing ring 112. The compressed region 122c is illustrated as compressed. Without the pull wire 116 in the opening 113 of the securing ring 112, the securing member 114 of the securing wire 120 is free to move through the opening 113 of the securing ring 112. The securing member 114 is no longer inhibiting the compressed portion 122c from elongating, and the securing member 114 begins to decompress. Expansion of the compressed portion 122c can push the securing ring 112 over the securing member 114.

FIG. 5E is an illustration of the compressed portion 122c elongated as a result of being free to decompress as described in relation to FIG. 5D. The distal portion 122c can elongate to push the securing ring 112 of the implant 102 distally. In some instances, the distal portion 122c can push the securing ring 112 with a force launch the securing ring 112 away from the distal end of the pusher tube 106 to create separation between the securing ring 112 and the pusher tube 106. The securing member 114 and lumen 107 of the pusher tube within the distal region 122c can be sized such that distal region 122c can elongate over the securing member 114, thereby moving the securing member 114 into the lumen 113 of the pusher tube 106.

FIGS. 6A through 6D are a sequence of illustrations during a treatment of an intravascular implant system 200 lacking a pusher tube.

FIG. 6A illustrates the implant 102 positioned within a microcatheter 104. The implant 102 can include a body 108 and securing ring 112 similar to as described elsewhere herein. The engagement/deployment system delivering the implant 102 through the microcatheter 104 can include a pull wire 116 similar to as described elsewhere herein and a securing wire 220. The securing wire 220, in addition to including a securing member 114 as described elsewhere herein can further include a pushing member 222 positioned in a proximal direction in relation to the securing ring 112. Configured as such, the engagement/deployment system need not include a pusher tube 106, 106a-c.

As illustrated, the pull wire 116 and securing wire 220 extend through the opening 113 of the securing ring 112. As illustrated in FIGS. 1B and 1C, the sum of the securing member diameter D2 and pull wire diameter D3 can be greater than the inner diameter D1 of the securing ring 112 to thereby inhibit the securing member 114 from passing through the opening 113 of the securing ring 112 when the pull wire 116 is in place through the securing ring 112. As illustrated in FIG. 6A, the pushing member 222 has a diameter D5 such that the sum of the pushing member diameter D5 and pull wire diameter D3 is greater than the inner diameter D1 of the securing ring 112 to thereby inhibit the pushing member 222 from passing through the inner diameter D1 of the securing ring 112. The securing member 114 and pusher member 222 are each inhibited from moving through the opening 113 in the securing ring 112 due to the extension of the pull wire 116 through the securing ring 112.

When the securing wire 220 is pushed distally, the pusher member 222 moves to engage the proximal surface SA2 of the securing ring 112.

FIG. 6B illustrates the implant 102 positioned within an aneurysm 50. At this and prior steps, the securing wire 220 can be moved proximally to translate the securing ring 112, and thereby a proximal portion 126 of the implant 102 proximally for repositioning and/or retraction of the implant 102. The securing member 114 can be moved to engage the distal surface SA3 of the securing ring 112 when the securing wire 220 is pulled proximally.

FIG. 6C illustrates the system 200 after the pull wire 116 is translatable in the proximal direction to exit the opening 113 in the securing ring.

FIG. 6D illustrates the securing wire 220 translated in the proximal direction to exit the opening 113 in the securing ring 112 when the pull wire 116 is absent from the opening 113.

The descriptions contained herein are examples of embodiments of the invention and are not intended in any way to limit the scope of the invention. As described herein, the invention contemplates many variations and modifications of the intravascular implant system, including alternative materials for component parts, and/or alternative geometries of component parts as would be apparent to those having ordinary skill in the art to which this invention relates and are intended to be within the scope of the claims which follow.

What is claimed is:

1. A system for deploying an intrasaccular implant to occlude an aneurysm, the system comprising:
   the intrasaccular implant comprising a securing ring thereon, the securing ring comprising a proximal surface and an opening comprising an inner diameter;
   a pusher tube comprising:
      a distal surface sized to engage the proximal surface of the securing ring and positioned to face the proximal surface of the securing ring;
      a flexible portion at a distal region of the pusher tube, the flexible portion comprising greater flexibility compared to a majority of the pusher tube; and
      a hypotube;
   a securing wire extending through a lumen of the pusher tube and the opening of the securing ring, the securing wire comprising an extended securing member thereon positioned on an opposite side of the securing ring in relation to the pusher tube, the securing member comprising a securing member diameter measuring less than the inner diameter of the opening of the securing ring; and
   a pull wire extending through the lumen of the pusher tube and the opening of the securing ring, the pull wire comprising a pull wire diameter such that the sum of the securing member diameter and the pull wire diameter measures greater than the inner diameter of the opening of the securing ring,
   wherein the pusher tube further comprises an extended pushing member formed on the securing wire in a proximal direction in relation to the securing member on the securing wire, and
   wherein the securing wire is coupled to an inner surface of the pusher tube by an attachment portion.

2. The system of claim 1, wherein the intrasaccular implant, pusher tube, securing wire, and pull wire are sized to fit within a microcatheter.

3. The system of claim 2, wherein the intrasaccular implant comprises a braided mesh that is self-expandable upon exiting the microcatheter.

4. The system of claim 1,
   wherein the opening of the securing ring comprises a substantially circular shape defined by the inner diameter,
   wherein the securing member comprises a substantially spherical shape defined by the securing member diameter, and
   wherein the pull wire comprises a substantially circularly shaped perimeter defined by the pull wire diameter.

5. The system of claim 1,
   wherein the pull wire is movable to exit the opening of the securing ring, and
   wherein the securing wire is movable to pass the securing member through the opening in the securing ring when the pull wire has exited the opening of the securing ring.

6. The system of claim 1,
   wherein the intrasaccular implant comprises a cavity therein, and
   wherein the securing member and a portion of the pull wire are disposed in the cavity of the intrasaccular implant.

7. The system of claim 1, wherein the pusher tube comprises a compressibly resilient portion at the distal region of the pusher tube.

8. The system of claim 7,
   wherein the securing member of the securing wire is engaged to the securing ring, and
   wherein the compressibly resilient portion is compressed due to tension in the securing wire over a portion of the securing wire extending from the securing ring to a coupling of the portion of the securing wire to the inner surface of the pusher tube.

9. The system of claim 7,
   wherein the pull wire is movable to exit the securing ring, and
   wherein the compressibly resilient portion is configured to expand and push the securing ring over the securing member when the pull wire has exited the securing ring.

10. A method of deploying an intrasaccular implant in an aneurysm, the method comprising:
    selecting a system comprising a microcatheter, a pusher tube, a securing wire comprising a radially extending securing member, a pull wire, and an intrasaccular implant comprising a securing ring;
    positioning the system in a delivery configuration such that the pusher tube, securing wire, pull wire, and implant are positioned within the microcatheter, the pusher tube is in a proximal direction in relation to the securing ring, the securing wire extends through the securing ring and pusher tube such that the securing member is positioned in a distal direction from the securing ring, and the pull wire extends through the pusher tube and the securing ring;
    moving the implant in the distal direction through the microcatheter by moving the pusher tube, pull wire, and securing wire in the distal direction;
    extending the intrasaccular implant into a sac of the aneurysm;
    retracting the pull wire in the proximal direction to free the pull wire from the securing ring; and retracting the securing wire from the securing ring by moving the securing member through the securing ring when the pull wire is free from the securing ring,
wherein the pusher tube comprises:
a distal surface sized to engage a proximal surface of the securing ring and positioned to face the proximal surface of the securing ring;
a flexible portion at a distal region of the pusher tube, the flexible portion comprising greater flexibility compared to a majority of the pusher tube;
a hypotube; and
an extended pushing member formed on the securing wire in a proximal direction in relation to the securing member on the securing wire,
wherein the securing wire is coupled to an inner surface of the pusher tube by an attachment portion.

11. The method of claim 10, wherein the step of extending the intrasaccular implant into the sac of the aneurysm further comprises allowing the implant to self-expand in the sac.

12. The method of claim 10, further comprising:
maintaining attachment of the implant to the pusher tube by engaging the securing member to a distal surface of the securing ring while engaging the distal surface of the pusher tube to the proximal surface of the securing ring.

13. The method of claim 12, wherein maintaining attachment of the implant to the pusher tube further comprises inhibiting the securing member from passing through the securing ring by maintaining the pull wire to extend within the securing ring.

14. The method of claim 13, wherein retracting the securing wire from the securing ring further comprises retracting the pusher tube in the proximal direction while the securing wire is coupled to the pusher tube.

15. An intravascular treatment system comprising:
an implant comprising an embolic body and a securing ring affixed to the body, the securing ring comprising a proximal surface, a distal surface, and an opening comprising an inner diameter;
a pusher tube;
a pull wire extending through the opening of the securing ring and comprising a pull wire diameter; and
a securing wire extending through the opening of the securing ring and comprising an extended securing member thereon and an extended pusher member thereon, the securing member positioned in a distal direction in relation to the distal surface of the securing ring and comprising a first diameter, the extended pusher member positioned in a proximal direction in relation to the proximal surface of the securing ring and comprising a second diameter, the first diameter dimensioned such that the sum of the pull wire diameter and first diameter is greater than the inner diameter of the securing ring, and the second diameter dimensioned such that the sum of the pull wire diameter and the second diameter is greater than the inner diameter of the securing ring,
wherein the pusher tube comprises:
a distal surface sized to engage the proximal surface of the securing ring and positioned to face the proximal surface of the securing ring;
a flexible portion at a distal region of the pusher tube, the flexible portion comprising greater flexibility compared to a majority of the pusher tube; and
a hypotube;
wherein the securing wire is coupled to an inner surface of the pusher tube by an attachment portion.

16. The system of claim 15,
wherein the securing member is movable to engage the distal surface of the securing ring when the securing wire is pulled proximally, and
wherein the pusher member is movable to engage the proximal surface of the securing ring when the securing wire is pushed distally.

17. The system of claim 15,
wherein the securing member and pusher member are each inhibited from moving through the opening in the securing ring due to the extension of the pull wire through the securing ring.

18. The system of claim 15,
wherein the pull wire is translatable in the proximal direction to exit the opening in the securing ring, and
wherein the securing wire is translatable in the proximal direction to exit the opening in the securing ring when the pull wire is absent from the opening.

* * * * *